United States Patent [19]

Mallams et al.

[11] 4,009,328
[45] Feb. 22, 1977

[54] AMINOGLYCOSIDE 66-40C, METHOD FOR ITS MANUFACTURE, METHOD FOR ITS USE AS AN INTERMEDIATE IN THE PREPARATION OF KNOWN ANTIBIOTICS AND NOVEL ANTIBACTERIALS

[75] Inventors: Alan K. Mallams, West Orange; Richard W. Tkach, Linden, both of N.J.; David Huw Davies, Macclesfield, England.

[73] Assignee: Schering Corporation, Kenilworth, N.J.

[22] Filed: May 2, 1975

[21] Appl. No.: 574,073

[52] U.S. Cl. .................. 536/17; 424/180; 536/10; 195/31 R
[51] Int. Cl.² .......................... C07H 15/22
[58] Field of Search ............ 260/210 AB, 210 NE, 260/210 K; 536/17

[56] References Cited

UNITED STATES PATENTS

| | | | |
|---|---|---|---|
| 3,651,042 | 3/1972 | Marquez et al. | 260/210 AB |
| 3,832,286 | 8/1974 | Weinstein et al. | 260/210 AB |
| 3,880,828 | 4/1975 | Mallams et al. | 260/210 AB |
| 3,929,762 | 12/1975 | Umezawa et al. | 260/210 AB |

FOREIGN PATENTS OR APPLICATIONS

| 1,033,394 | 6/1966 | United Kingdom | 260/210 AB |
|---|---|---|---|

*Primary Examiner*—Johnnie R. Brown
*Attorney, Agent, or Firm*—Mary S. King; Stephen B. Coan

[57] ABSTRACT

Aminoglycoside 66-40C, a minor product produced by the fermentation of *Micromonospora inyoensis*, is separated from said fermentation mixture, and is used as an intermediate in preparing the known antibiotic, sisomicin, as well as 6'-N-alkylsisomicins having antibacterial activity. Claimed are Aminoglycoside 66-40C as well as 6'-N-t-alkylsisomicins having a tertiary carbon bonded to the 6'-nitrogen.

11 Claims, No Drawings

AMINOGLYCOSIDE 66-40C, METHOD FOR ITS MANUFACTURE, METHOD FOR ITS USE AS AN INTERMEDIATE IN THE PREPARATION OF KNOWN ANTIBIOTICS AND NOVEL ANTIBACTERIALS

FIELD OF THE INVENTION

This invention relates to a novel composition of matter, to a method for its manufacture, to a method for its use in the manufacture of known antibiotics and of novel antibacterial agents.

More specifically, this invention relates to Aminoglycoside 66–40C, to the method for its manufacture, and to its use as a starting material in the process for the manufacture of known antibiotics and novel antibacterial agents.

In particular, this invention relates to the conversion of Aminoglycoside 66–40C, to sisomicin and to 6′-N-alkylsisomicins having antibacterial activity, including novel 6′-N-t-alkylsisomicins, e.g. 6′-N-t-butylsisomicin.

This invention also relates to processes for preparing 6′-N-t-alkylsisomicins and to the method of using said 6′-N-t-alkylsisomicins as antibacterial agents.

PRIOR ART

It is known in the art that submerged fermentation of *Micromonospora inyoensis* (NRRL 3292) produces the antibiotic sisomicin as the principal product of the fermentation together with coproduced minor components identified as garamine, Antibiotic 66-40B and Antibiotic 66-40D.

By the present invention there has been discovered and characterized a novel aminoglycoside identified as Aminoglycoside 66-40C, which is coproduced in the fermentation of *Micromonospora inyoensis*. A method of isolating Aminoglycoside 66-40C from the fermentation mixture has been developed as well as a process for converting Aminoglycoside 66-40C to known antibiotics such as sisomicin and Antibiotic G-52 or to novel 6′-N-alkylsisomicins having antibacterial activity of which 6′-N-alkylsisomicins having a tertiary carbon bonded to the 6′-nitrogen are the compounds of this invention.

GENERAL DESCRIPTION OF THE INVENTION

Composition-of-Matter Aspect

In one of its composition-of-matter aspects, this invention relates to Aminoglycoside 66-40C having a novel dimeric structure containing $\alpha,\beta$-unsaturated imine groups not previously encountered in known aminoglycosides. Aminoglycoside 66-40C is represented by the following formula I:

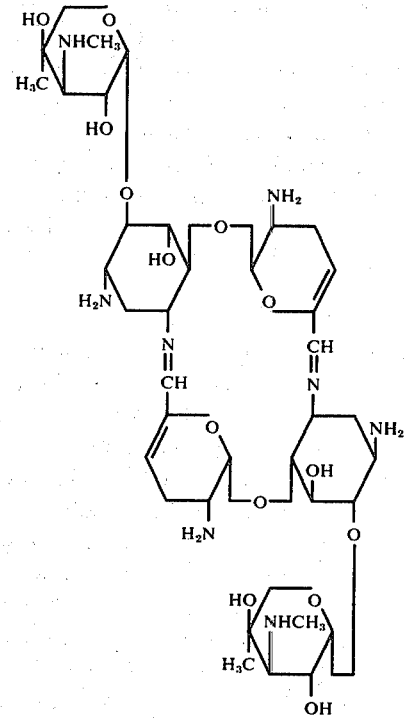

Aminoglycoside 66-40C of this invention is characterized as a colorless, amorphous solid, which is soluble in water, alcohols, and is particularly soluble in dimethylformamide.

In a second composition-of-matter aspect, this invention relates to novel 6′-N-t-alkylsisomicins produced herein, said compounds being represented by the following formula II:

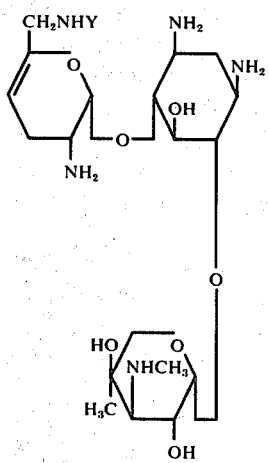

wherein Y is an alkyl substituent having up to 8 carbon atoms and having a tertiary carbon atom bonded to the 6′-nitrogen. This invention also includes pharmaceutically acceptable acid addition salts of the 6′-N-alkyl derivatives of formula II.

The 6′-N-t-alkylsisomicins of this invention are characterized as colorless, amorphous solids which are soluble in water, alcohols, and are partially soluble in dimethylformamide.

Also included in the composition-of-matter aspect of this invention are the acid addition salts of 6'-N-t-alkylsisomicins. These salts are prepared according to known procedures such as by neutralizing the free base with the appropriate acid, usually to about pH 5. Suitable acids for this purpose include acids such as hydrochloric, sulfuric, phosphoric, hydrobromic and the like.

The acid addition salts of the 6'-N-t-alkylsisomicins are characterized by being white solids which are soluble in water and insoluble in most polar and non-polar organic solvents.

The 6'-N-t-alkylsisomicins of this invention and their pharmaceutically acceptable acid addition salts (e.g. 6'-N-t-butylsisomicin and the sulfate salts thereof) exhibit a spectrum of antibacterial activity *in vitro* against gram-positive bacteria, e.g. *Staphylococcus aureus* (strains 209P, Wood, Ziegler and 59N); *Bacillus subtilis* (strain 6633); and *Streptococcus pyogenes* (strain Group A Cruz). The 6'-N-t-alkylsisomicins of this invention such as 6'-N-t-butylsisomicin and the pharmaceutically acceptable acid addition salts thereof also exhibit antibacterial activity *in vitro* against gram-negative bacteria, e.g. *Escherichia coli* (strains ATCC 10536, St. M. 589, C-13, Baker 2, F14-BK, St. M. 1574-1); *Pseudomonas aeruginosa* (strains St. M. 1262, NRRL 3223, Stone 20 and Stone 39), *Proteus mirabilis* (strain Harding) and *Serratia marcescens* (strain Dalton) and *Salmonella typhimurium* (strain Group B) and *Klebsiella pneumoniae* (strains Alder 17, 18 and 22). Thus the compounds of our invention may be used to "sterilize" equipment such as in operating rooms and in hospital wards.

PROCESS ASPECT OF THE INVENTION

A process aspect of this invention relates to the process which comprises separating Aminoglycoside 66-40C from a mixture containing Aminoglycoside 66-40C, Antibiotic 66-40B, Antibiotic 66-40D and garamine by a. dissolving the mixture in a solvent system consisting of chloroform, methanol and 7% ammonium hydroxide in the volume ratio of 1:2:1, b. adsorbing the resulting solution on silica gel, c. selectively desorbing said Aminoglycoside 66-40C from the silica gel using the same solvent as in (a), d. isolating the Aminoglycoside 66-40C from the solution, and e. passing the Aminoglycoside 66-40C down Amberlite IRA 401S (OH⁻) resin to obtain Aminoglycoside 66-40C free from coproduced substances.

The starting material for this process is a crude mixture of minor components obtained from the fermentation of *Micromonospora inyoensis* and isolated from the fermentation in the manner described in Preparation I.

In another process aspect of this invention Aminoglycoside 66-40C is converted to sisomicin and to 6'-N-X-sisomicins. The 6'-N-X-sisomicins prepared by this process are represented by the following formula III:

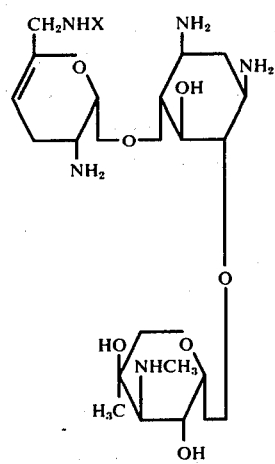

wherein X is an alkyl substituent selected from the group consisting of alkyl, alkenyl, cycloalkyl, hydroxyalkyl, aminoalkyl, alkylaminoalkyl, aminohydroxyalkyl and alkylaminohydroxyalkyl, said alkyl substituent having up to 8 carbon atoms. When said alkyl substituent is substitued by both hydroxyl and amino functions, only one of said functions can be attached at any one carbon atom.

Our process whereby the 6'-N-X-sisomicins of formula III are prepared comprises reaction of Aminoglycoside 66-40C in a lower alkanol with ammonia or a primary amine having the formula X-NH$_2$, X being defined hereinabove; followed by the reaction in situ of the intermediate thereby formed with a hydride-donor reducing agent.

When Aminoglycoside 66-40C is dissolved in a lower alkanol, the reaction with ammonia or a primary amine is preferentially carried out in the presence of an acid catalyst. Acids useful in our process include mineral acids such as hydrochloric, sulfuric, phosphoric and the like, preferably phosphoric acid. Hydride-donor reducing agents useful in our process are selected from the group consisting of sodium borohydride, lithium cyanoborohydride, sodium cyanoborohydride, morpholinoborane, dialkylaminoborane and tetraalkylammonium cyanoborohydride.

Usually, our process is carried out in the temperature range from about 70° C to about 150° C utilizing about a 10 molar excess of ammonia or a primary amine.

By our process, when Aminoglycoside 66-40C is treated with, for example, ammonia, methylamine, phenethylamine, there is obtained, respectively, sisomicin, Antibiotic G-52 and 6'-N-phenethylsisomicin. When the primary amine has an alkyl substituent having up to 8 carbon atoms which has a tertiary carbon atom bonded to the 6'-nitrogen, our process produces a 6'-N-t-alkyl compound of our invention. For example, when Aminoglycoside 66-40C is treated with tertiary butylamine there is produced 6'-N-t-butylsisomicin of this invention.

When carrying out our process utilizing a primary amine (i.e. X-NH$_2$) wherein the alkyl substituent (X) is an aminoalkyl or an aminohydroxyalkyl, the amine groups must be protected prior to reaction with Aminoglycoside 66-40C; the hydroxyl functions may be protected although this is not necessary. For example, when preparing 6'-N-(β-hydroxy-δ-aminobutyl)sisomicin the requisite starting material is 4-acetamido-2- acetoxybutylamine, which is prepared by treating 4,4-diethoxy-3-hydroxybutylamine with acetic anhydride, hydrolyzing the resultant 4,4-diethoxy-3-acetoxy-1-acetamido-1-acetamidobutane and subjecting the thereby formed 4-acetamido-2-acetoxybutanal to reductive amination to obtain 4-acetamido-2-acetoxybutylamine. Reaction of the foregoing intermediate with Aminoglycoside 66-40C produces 6'-N-(β-acetoxy-δ-acetamidobutyl)sisomicin which upon reaction with 10% aqueous potassium hydroxide at elevated temperatures yields 6'-N-(β-hydroxy-δ-aminobutyl)-sisomicin.

In general, 6'-N-alkylsisomicin intermediates wherein amino and/or hydroxyl groups are protected by functional groups must be further reacted to "deprotect" said hydroxyl or amino groups, e.g. with a base such as 10% aqueous potassium hydroxide or 5% aqueous sodium hydroxide.

The invention described hereinabove is illustrated in detail hereinbelow in the Preparations and Examples which should not be construed as limiting the scope of our invention.

PREPARATION I

Crude Mixture of the Minor Components of the Fermentation of Micromonospora inyoensis The crude antibiotic complex produced by the fermentation of *Micromonospora inyoensis* (ref. British Patent No. 1,274,518) is subjected to chromatographic separation on silica gel. The complex is dissolved in the lower phase of a solvent mixture consisting of chloroform, methanol and concentrated ammonium hydroxide (1:1:1). Add this solution to the silica gel column and elute the column with the same solvent mixture. Collect the fractions of eluant and monitor the fractions by thin-layer chromatography on silica gel plates using the same solvent system as that used on the column. Combine the fractions containing material having the same mobility on thin layer and evaporate the fractions to dryness to obtain two fractions of active material. The first (least polar) fraction eluted contains substantially pure sisomicin and the last (most polar) fraction contains the crude mixture of the minor components of the fermentation.

PREPARATION II

4-Phthalimidobutylamine

Protect the amino function in 4,4-diethoxybutylamine by conversion thereof to a phthalimido function. Hydrolyze the resultant 1-phthalimido-4,4-diethoxybutane with 1N aqueous sulfuric acid at 25° C to obtain 4-phthalimidobutanal. Subject the compound to reductive amination using ammonium chloride and sodium cyanoborohydride in aqueous methanol at 25° C to obtain 4-phthalimidobutylamine.

PREPARATION III

4-Acetamido-2-acetoxybutylamine

Treat 4,4-diethoxy-3-hydroxybutylamine with acetic anhydride in pyridine to obtain 4,4-diethoxy-3-acetoxy-1-acetamido butane. Hydrolyze with 1N aqueous sulfuric acid at 25° to obtain 4-acetamido-2-acetoxybutanal. Subject to reductive amination in aqueous methanol using ammonium chloride and sodium cyanoborohydride at 25° C to obtain 4-acetamido-2-acetoxybutylamine.

PREPARATION IV

4-(N-Methylacetamido)-2-acetoxybutylamine

Treat 4,4-diethoxy-3-hydroxybutylamine with acetic anhydride in pyridine to obtain 4,4-diethoxy-3-acetoxy-1-acetamido butane. Treat with sodium hydride and methyl iodide to obtain 1-(N-methylacetamido)-3-acetoxy-4,4-diethoxybutane. In a similar manner to that described in Preparation II hydrolyze with sulfuric acid, reductively aminate the resulting 4-(N-methylacetamido)-2-acetoxybutanal to obtain the resulting 4-(N-methylacetamido)-2-acetoxybutylamine.

EXAMPLE I

Aminoglycoside 66-40C

To a chromatographic column of about 160 cm. in length by about 5 cm. in diameter containing silica gel, add 9.65 g. of the crude mixture of the minor components of the fermentation of *Micromonospora inyoensis* dissolved in a solution of chloroform- methanol - 7% ammonium hydroxide (1:2:1). Elute the column with the same solvent system, evaporate the eluates, and pass an aqueous solution of the resultant residue down a column of Amberlite IRA 401S (OH$^-$) resin. Lyophilize the combined eluates to obtain a residue of (1.8 g.) of Aminoglycoside 66-40C as a colorless amorphous solid; m.p.: 185°–205° C; m/e 856 (M+) MW 847 (osmometry) (calc. MW 856); $[\alpha]_D^{26}$ + 112.5°, (c 0.3%, H$_2$O); I.R.: $\nu$ max (KCl) 3300, 1670, 1640, 1620, 1025 cm$^{-1}$; U.V.: $\lambda$ max(CH$_3$OH) 248 m$\mu$ ($\epsilon$ 22,000); C.D.: $[\theta]_{280}$ −7,720 (CH$_3$OH) $[\theta]_{290}$ −23,400 (TACu); $[\theta]_{290}$ −18,620 (Cupra A); NMR: $\delta$(D$_2$O) 1.22 (6H, s,4''-CH$_3$), 2.52 (6H,s,3''-NCH$_3$), 5.15 (2H,d,J4H$_z$,H$_1$''), 5.48 (2H, m, H$_4$'), 5.50 (2H, d, J$_2$H$_z$, H$_1$') and 7.56 ppm. (2H, s, H$_6$').

EXAMPLE II

Sisomicin

Dissolve 100 mg. of Aminoglycoside 66-40C in 3 ml. of methanol at room temperature, then saturate the solution with ammonia gas. Heat the solution in a sealed vessel at 75° C for 14 hours, cool, then add 300 mg. of sodium borohydride and stir the mixture for 30 minutes at about 25° C. Evaporate the solution and chromatograph the resulting residue on a silica gel column eluting with the lower phase of a chloroform - methanol - concentrated ammonium hydroxide solution (1:1:1). Evaporate the combined eluates to a residue comprising sisomicin. Purify by passing an aqueous solution of the sisomicin down a column of Amberlite IRA 401S (OH$^-$) resin and then lyophilize to obtain sisomicin 40 mg; $[\alpha]_D^{26}$ + 186.0° (c 0.3%, H$_2$O).

EXAMPLE III

Antibiotic G-52

Dissolve 100 mg. of Aminoglycoside 66-40C in 3 ml. ethanol and saturate the solution at room temperature with methylamine. Add 3 drops of phosphoric acid to the mixture and heat in a sealed vessel at about 100° C for 16 hours. Cool, add 400 mg. of sodium borohydride and stir the mixture at about 25° C for 30 minutes. Pass the mixture through Amberlite IRA 401S (OH$^-$) resin. Concentrate the eluant and chromatograph the residue on a silica gel column using the lower phase of a chloroform-methanol-concentrated ammonium hydroxide solution (1:1:1) as the eluant. Concentrate the eluates and dissolve the residue in water and pass the aqueous solution down a column of Amberlite IRA-401S (OH⁻) resin and lyophilize to obtain a residue (32 mg.) of Antibiotic G-52; $[\alpha]_D^{26}$ + 147.5° (c 0.3%, H$_2$O).

EXAMPLE IV

Preparation of 6'-N-t-Butylsisomicin

Dissolve 100 mg. of Aminoglycoside 66-40C in a mixture of 1 ml. of ethanol and 2 ml. t-butylamine. Add 4 drops of phosphoric acid and heat the mixture in a sealed vessel at about 120° C for 15 hours. Cool the reaction mixture, add 50 mg. sodium borohydride and stir at 25° C for 30 minutes. Pass the mixture through Amberlite IRA 401S (OH⁻) resin and concentrate to a residue. Chromatograph the residue on a silica gel column eluting with the lower phase of a chloroform-methanol-concentrated ammonium hydroxide solution (1:1:1). Concentrate the eluates to a residue and dissolve said residue in water and pass the aqueous solution down a column of Amberlite IRA 401S (OH⁻) resin and then lyophilize to obtain a residue (20 mg.) of 6'-N-t-butylsisomicin. m.p.: 125°–130° C; $[\alpha]_D^{26}$ + 136.1°(c 0.3%, H$_2$O I.R.: $\nu$ max(KCL)3350, 2950, 1690, 1070, cm.⁻¹; m/e 503 (M ⁺); N.M.R.: $\delta$(D$_2$)1.21(12H,s, (CH$_3$)$_4$ C-and 4''–CH$_3$), 2.52(3H,s,3''-NCH$_3$), 3.32(2H,s,H$_6$'), 4.99(1H,m,H$_4$'),5.07 (1H,d,J 4Hz,H$_1$'') and 5.34 ppm. (1H,d,J 2Hz,H$_1$').

EXAMPLE V

6'-N-(2-Phenylethyl)-sisomicin

Dissolve 500 mg. of Aminoglycoside 66-40C in a solution of 7 ml. of 2-phenylethylamine and 7 ml. of ethanol, add 2 drops of phosphoric acid and heat in a sealed vessel at 70° C for 16 hours and then at 100° C for 5 hours. Cool the solution and add 500 mg. of sodium borohydride and stir for 1 hour at 25° C. Pass the solution through Amberlite IRA 401S (OH⁻) resin and extract the aqueous solution with benzene. Adjust the pH of the aqueous layer to 9 by the addition of acetic acid. Re-wash the benzene extract with water and combine the water wash with the previous aqueous extract and evaporate. Chromatograph the resulting residue on a silica gel column eluting with the lower phase of a chloroform-methanol-concentrated ammonium hydroxide solution (2:1:1). Concentrate the eluates and dissolve the residue in water and pass down a column of Amberlite IRA 401S (OH⁻) resin and lyophilize to obtain a residue of (67 mg) 6'-N-(2-phenylethyl)-sisomicin; $[\alpha]_D^{26}$ + 137.7° (c 0.3%,H$_2$O); C.D.: $[\theta]_{288}$ −8,230 (TACu); $[\theta]_{290}$ −6,620 (Cupra A); I.R.: $\nu$ max (KBr) 3300, 1650, 1055, 1030 cm⁻¹; N.M.R.: $\delta$(D$_2$O)1.15(3H,s,4''-CH$_3$), 2.47(3H,s,3''-NCH$_3$), 2.77 (4H,s,6'-NCH$_2$CH$_2$ C$_6$H$_5$), 3.11 (2H,s,6'-CH$_2$), 4.79(1H,m,H$_4$'), 5.03 (1H,d,J 4Hz, H$_1$ ''), 5.20 (1H,d,J 2Hz, H$_1$'), 7.30 and 7.32 ppm (5H,s, —C$_6$H$_5$);m/e 551.3333.(M.⁺) (C$_{27}$H$_{45}$N$_5$O$_7$ requires: m/e 551.3319).

EXAMPLE VI

6'-N-X-sisomicins

In a manner similar to that described in Example V react Aminoglycoside 66-40C with an equivalent quantity of each of the following amines:
a. ethylamine
b. isopropylamine
c. cyclopropylmethylamine
d. ethanolamine
e. allylamine and isolate the resultant products to obtain respectively:
f. 6'-N-ethylsisomicin
g. 6'N-isopropylsisomicin
h. 6'-N-cyclopropylmethylsisomicin
i. 6'-N-($\beta$-hydroxyethyl)sisomicin
j. 6'-N-allylsisomicin

EXAMPLE VII

6'-N-($\delta$-aminobutyl)sisomicin a. In a manner similar to that described in Example V react Aminoglycoside 66-40C with an equivalent quantity of 4-phthalimidobutylamine. Isolate the resultant product to obtain 6'-N-($\delta$-phthalimidobutyl)-sisomicin.

b. To 0.5 g. of 6'-N($\delta$-phthalimidobutyl)-sisomicin add 5 ml. of 5% ethanolic hydrazine hydrate and heat under reflux for 13 hours. Pour the reaction solution into a large volume of tetrahydrofuran and collect by filtration the resulting precipitate comprising 6'-N-($\delta$-aminobutyl)-sisomicin.

EXAMPLE VIII

6'-N-($\beta$-hydroxy-$\delta$-aminobutyl)sisomicin a. In a manner similar to that described in Example V react Aminoglycoside 66 40C with an equivalent quantity of 4-acetamido-2-acetoxybutylamine. Isolate the resultant product to obtain 6'-N-($\beta$-acetoxy-$\delta$-acetamidobutyl)-sisomicin.

b. Heat a mixture of 6'-N-($\beta$-acetoxy-$\delta$-acetamidobutyl)-sisomicin in 10% aqueous potassium hydroxide at 100° C for 13 hours, pass the mixture down a column of Amberlite IRC-50(H+)ion exchange resin and elute with 2N aqueous ammonium hydroxide. Concentrate the eluant and dissolve the resultant residue in water and lyophilize to obtain a residue comprising 6'-N($\beta$-hydroxy-$\delta$-aminobutyl)-sisomicin.

EXAMPLE IX

6'-N-[$\beta$-hydroxy-$\delta$-(methylamino)butyl]-sisomicin a. In a manner similar to that described in Example V treat Aminoglycoside 66-40C with an equivalent quantity of 4-(N-methylacetamido)-2-acetoxybutylamine. Isolate the resultant product to obtain a residue comprising 6'-N-[$\delta$-(N-methylacetamido)-$\beta$-acetoxybutyl]-sisomicin.

b. In a manner similar to Example VIIIb treat 6'-N-[$\delta$-(N-methylacetamido)-$\beta$-acetoxybutyl]-sisomicin with 10% aqueous potassium hydroxide and isolate the resultant product to obtain 6'-N-[$\beta$-hydroxy-$\delta$-(methylamino)butyl]-sisomicin.

EXAMPLE X

Preparation of Acid Addition Salts

A. Sulfate salts (Sulfuric Acid Addition Salts)

Dissolve 5.0 g. of 6'-N-t-butylsisomicin in 25 ml. of water and adjust the pH of the solution to 4.5 with 1N sulfuric acid. Pour into about 300 ml. of methanol with vigorous agitation, continue the agitation for about 10–20 minutes and filter. Wash the precipitate with methanol and dry at about 60° in vacuo to obtain 6'-N-t-butylsisomicin sulfate.

B. Hydrochloride Salts

Dissolve 5.0 g. of 6'-N-t-butylsisomicin in 2.5 ml. of water. Acidify with 2N hydrochloric acid to pH 5. Lyophilize to obtain 6'-N-t-butylsisomicin hydrochloride.

We claim:

1. Aminoglycoside 66-40C, having the following structural formula:

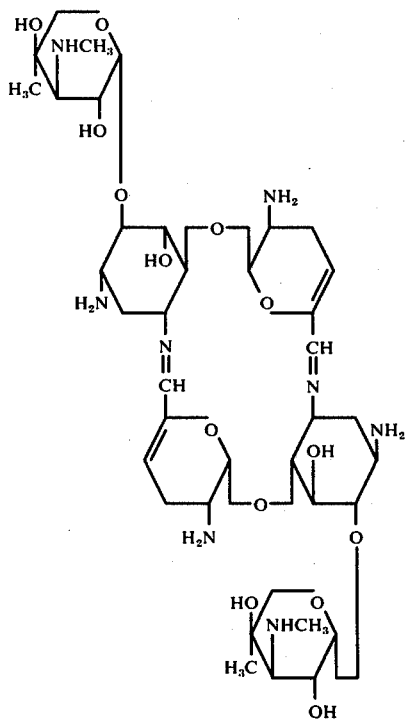

and being free of substances co-produced therewith.

2. The process which comprises separating Aminoglycoside 60-40C from a mixture containing Aminoglycoside 66-40C, Antibiotic 66-40B, Antibiotic 66-40D and garamine by (a) dissolving the mixture in a solvent system consisting of chloroform, methanol and 7% ammonium hydroxide in the volume ratio 1:2:1 (b) absorbing the resulting solution on silica gel (c) selectively desorbing said Aminoglycoside 66-40C from the silica gel using the same solvent as in (a), (d) isolating the Aminoglycoside 66-40C from the solution by evaporation of said solvent, and (e) passing an aqueous solution of the Aminoglycoside 66-40C down Amberlite IRA-401S (OH⁻) resin and lyophilizing to obtain Aminoglycoside 66-40C free from co-produced substances.

3. The process for the preparation of sisomicin and 6'-N-X-sisomicin wherein X is an alkyl substituent selected from the group consisting of alkyl, alkenyl, cycloalkyl, hydroxyalkyl, aminoalkyl, alkylaminoalkyl, aminohydroxyalkyl and alkylaminohydroxyalkyl said alkyl substituent having up to 8 carbon atoms and when said alkyl substituent is substituted by both hydroxyl and amino functions, only one of said functions can be attached at any one carbon atoms, which comprises the reaction of Aminoglycoside 66-40C in a lower alkanol with ammonia or a primary amine having the formula X-NH₂ wherein X is as defined hereinabove, followed by the reaction in situ of the intermediate thereby formed with a hydride donor reducing agent selected from the group consisting of sodium borohydride, lithium cyanoborohydride and sodium cyanoborohydride, morpholinoborane, dialkylaminoborane, tetraalkylammonium cyanoborohydride.

4. The process of claim 3 wherein the step of reacting Aminoglycoside 66-40C with ammonia or a primary amine, X-NH₂ as previously defined, is carried out in the presence of an acid.

5. The process of claim 3 when carried out at temperatures in the range of from about 70° C to about 150° C.

6. The process of claim 3 wherein Aminoglycoside 66-40C is reacted with about a 10 molar excess of ammonia or a primary amine X-NH₂ as previously defined, in the temperature range of from about 70° C to about 150° C.

7. The process of claim 3 for the preparation of sisomicin which comprises:
the reaction of Aminoglycoside 66-40C with at least a 10 molar excess of ammonia in a lower alkanol at about 75° C in a sealed vessel, followed by the reaction of the thereby formed intermediate in situ with sodium borohydride.

8. The process of claim 4 for the preparation of Antibiotic G-52 which comprises:
the reaction of Aminoglycoside 66-40C with about a 10 molar excess of methylamine in a lower alkanol in the presence of phosphoric acid at about 100° C in a sealed vessel, followed by the reaction of the thereby formed intermediate in situ with sodium borohydride.

9. A compound selected from the group consisting of 6'-N-Y-sisomicin wherein Y is an alkyl substituent having 4 to 8 carbon atoms and having a tertiary carbon atom bonded to the 6'-nitrogen, and the pharmaceutically acceptable acid addition salts thereof.

10. A compound of claim 9 which is 6'-N-t-butylsisomicin.

11. The process of claim 4 for the preparation of 6'-N-t-butylsisomicin which comprises:
the reaction of Aminoglycoside 66-40C with about a 10 molar excess of t-butylamine in a lower alkanol in the presence of phosphoric acid at about 120° C in a sealed vessel, followed by the reaction of the thereby formed intermediate in situ with sodium borohydride.

* * * * *